(12) United States Patent
Sapienza et al.

(10) Patent No.: US 10,898,196 B2
(45) Date of Patent: Jan. 26, 2021

(54) CLEANING APPARATUS FOR SURGICAL INSTRUMENTS

(71) Applicant: Covidien LP, Mansfield, MA (US)

(72) Inventors: Jonathan W. Sapienza, Orange, CT (US); Paul D. Richard, Shelton, CT (US); Ramiro Cabrera, Cheshire, CT (US); Stephen R. Paul, East Hartford, CT (US)

(73) Assignee: Covidien LP, Mansfield, MA (US)

( * ) Notice: Subject to any disclaimer, the term of this patent is extended or adjusted under 35 U.S.C. 154(b) by 1327 days.

(21) Appl. No.: 14/829,771

(22) Filed: Aug. 19, 2015

(65) Prior Publication Data

US 2016/0143641 A1    May 26, 2016

Related U.S. Application Data

(60) Provisional application No. 62/082,643, filed on Nov. 21, 2014.

(51) Int. Cl.
| | | |
|---|---|---|
| *A61B 17/115* | (2006.01) | |
| *A61B 17/068* | (2006.01) | |
| *A61B 90/70* | (2016.01) | |
| *A61B 1/12* | (2006.01) | |
| *B08B 9/00* | (2006.01) | |

(Continued)

(52) U.S. Cl.
CPC .......... *A61B 17/115* (2013.01); *A61B 1/122* (2013.01); *A61B 1/125* (2013.01); *A61B 17/068* (2013.01); *A61B 90/70* (2016.02); *B08B 9/00* (2013.01); *A61B 17/1155* (2013.01);

(Continued)

(58) Field of Classification Search
None
See application file for complete search history.

(56) References Cited

U.S. PATENT DOCUMENTS 3,388,847 A    6/1968  Kasulin et al.
3,552,626 A    1/1971  Astafiev et al.
(Continued)

FOREIGN PATENT DOCUMENTS

CA    908529 A     8/1972
CA    1136020 A1   11/1982
(Continued)

OTHER PUBLICATIONS

European Search Report, dated Apr. 28, 2016, corresponding to European Application No. 15195534.1; 10 pages.

(Continued)

*Primary Examiner* — Hemant Desai
*Assistant Examiner* — Tanzim Imam
(74) *Attorney, Agent, or Firm* — Carter, DeLuca & Farrell LLP

(57) ABSTRACT

An apparatus for cleaning a surgical instrument includes an elongate member having a first end and a second end configured for disposal within a cavity of a surgical instrument. The elongate member defines a longitudinal channel and a plurality of apertures extending transversely through the elongate member. The apertures are in communication with the longitudinal channel. The first end of the elongate member is configured to be coupled to a source of fluid such that fluid passes through the longitudinal channel and out of the elongate member through the plurality of apertures.

14 Claims, 7 Drawing Sheets

(51) Int. Cl.
*A61B 17/00* (2006.01)
*B05B 13/06* (2006.01)

(52) U.S. Cl.
CPC .......... *A61B 2017/0046* (2013.01); *A61B 2017/00473* (2013.01); *A61B 2090/701* (2016.02); *B05B 13/0627* (2013.01)

(56) References Cited

U.S. PATENT DOCUMENTS

| | | | |
|---|---|---|---|
| 3,638,652 A | 2/1972 | Kelley | |
| 3,952,341 A | * 4/1976 | Cain | E03C 1/30 222/215 |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,646,745 A | 3/1987 | Noiles | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,754,909 A | 7/1988 | Barker et al. | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,445,644 A | 8/1995 | Pietrafitta et al. | |
| 5,447,514 A | 9/1995 | Gerry et al. | |
| 5,454,825 A | 10/1995 | Van Leeuwen et al. | |
| 5,470,006 A | 11/1995 | Rodak | |
| 5,474,223 A | 12/1995 | Viola et al. | |
| 5,497,934 A | 3/1996 | Brady et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,632,433 A | 5/1997 | Grant et al. | |
| 5,639,008 A | 6/1997 | Gallagher et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,758,814 A | 6/1998 | Gallagher et al. | |
| 5,799,857 A | 9/1998 | Robertson et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,279,809 B1 | 8/2001 | Nicola | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicola | |
| 6,533,157 B1 | 3/2003 | Whitman | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,595,887 B2 | 7/2003 | Thoma | |
| 6,601,749 B2 | 8/2003 | Sullivan et al. | |
| 6,605,078 B2 | 8/2003 | Adams | |
| 6,623,227 B2 | 9/2003 | Scott et al. | |
| 6,626,921 B2 | 9/2003 | Blatter et al. | |

(56) References Cited

U.S. PATENT DOCUMENTS

| | | | |
|---|---|---|---|
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,716,222 B2 | 4/2004 | McAlister et al. | |
| 6,716,233 B1 | 4/2004 | Whitman | |
| 6,742,692 B2 | 6/2004 | Hartwick | |
| 6,763,993 B2 | 7/2004 | Bolduc et al. | |
| 6,769,590 B2 | 8/2004 | Vresh et al. | |
| 6,945,444 B2 | 9/2005 | Gresham et al. | |
| 6,959,851 B2 | 11/2005 | Heinrich | |
| 7,059,331 B2 | 6/2006 | Adams et al. | |
| 7,063,095 B2* | 6/2006 | Barcay | B08B 9/00 134/166 R |
| 7,168,604 B2 | 1/2007 | Milliman et al. | |
| 7,303,106 B2 | 12/2007 | Milliman et al. | |
| 7,325,713 B2 | 2/2008 | Aranyi | |
| RE40,237 E | 4/2008 | Bilotti et al. | |
| 7,364,060 B2* | 4/2008 | Milliman | A61B 17/068 227/175.1 |
| 7,399,305 B2 | 7/2008 | Csiky et al. | |
| 7,401,722 B2 | 7/2008 | Hur | |
| 7,407,075 B2 | 8/2008 | Holsten et al. | |
| 7,686,800 B2* | 3/2010 | Savage | A61M 25/007 604/264 |
| 7,802,712 B2 | 9/2010 | Milliman et al. | |
| 2003/0225411 A1 | 12/2003 | Miller | |
| 2008/0221580 A1* | 9/2008 | Miller | A61B 10/025 606/80 |
| 2011/0082387 A1* | 4/2011 | Miller | A61B 10/025 600/567 |

FOREIGN PATENT DOCUMENTS

| | | | |
|---|---|---|---|
| DE | 1057729 B | 5/1959 | |
| DE | 19510707 A1 | 9/1996 | |
| DE | 102005048211 A1 | 4/2007 | |
| DE | 102010008745 A1 * | 8/2011 | A61B 90/70 |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 2105106 A1 | 9/2009 | |
| FR | 1136020 A | 5/1957 | |
| FR | 1461464 A | 2/1966 | |
| FR | 1588250 A | 4/1970 | |
| JP | 2003520080 A | 7/2003 | |
| JP | 2004121832 A | 4/2004 | |
| JP | 2011016084 A | 1/2011 | |
| WO | 01/51116 A2 | 7/2001 | |

OTHER PUBLICATIONS

European Communication dated Feb. 16, 2017, corresponding to European Application No. 15 195 534.1; 4 pages.

English translation of Japanese Office Action dated Aug. 28, 2019, corresponding to counterpart Japanese Application No. 2015-224597; 9 total pages.

Japanese Office Action dated May 28, 2019, issued in JP Appln. No. 2015-224597.

* cited by examiner

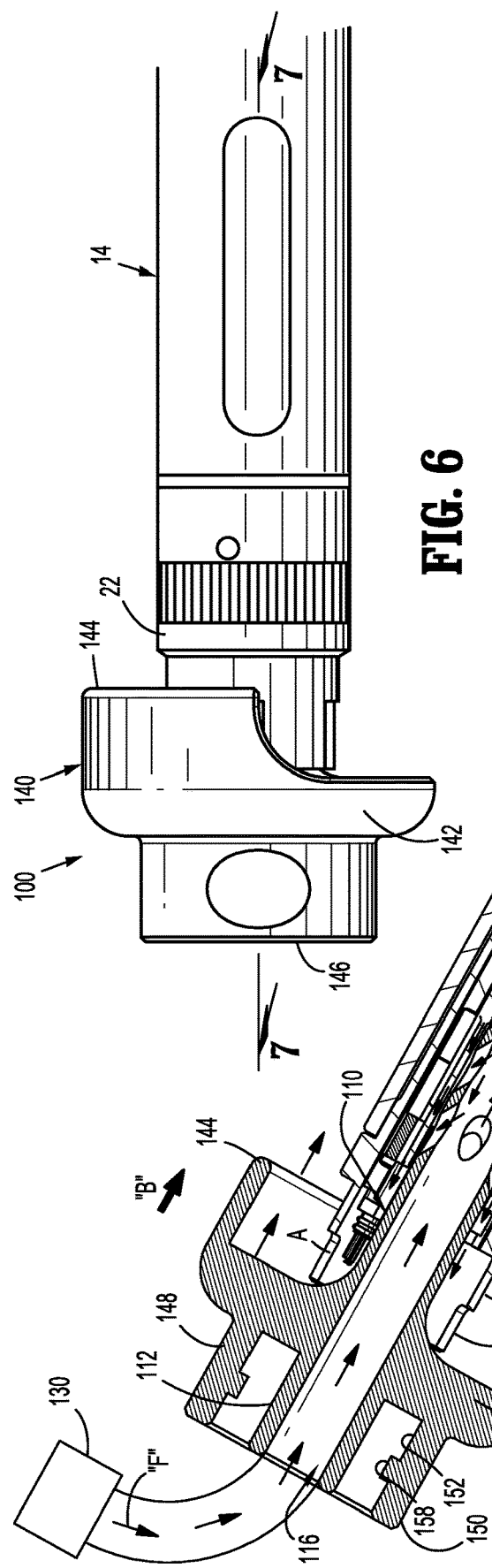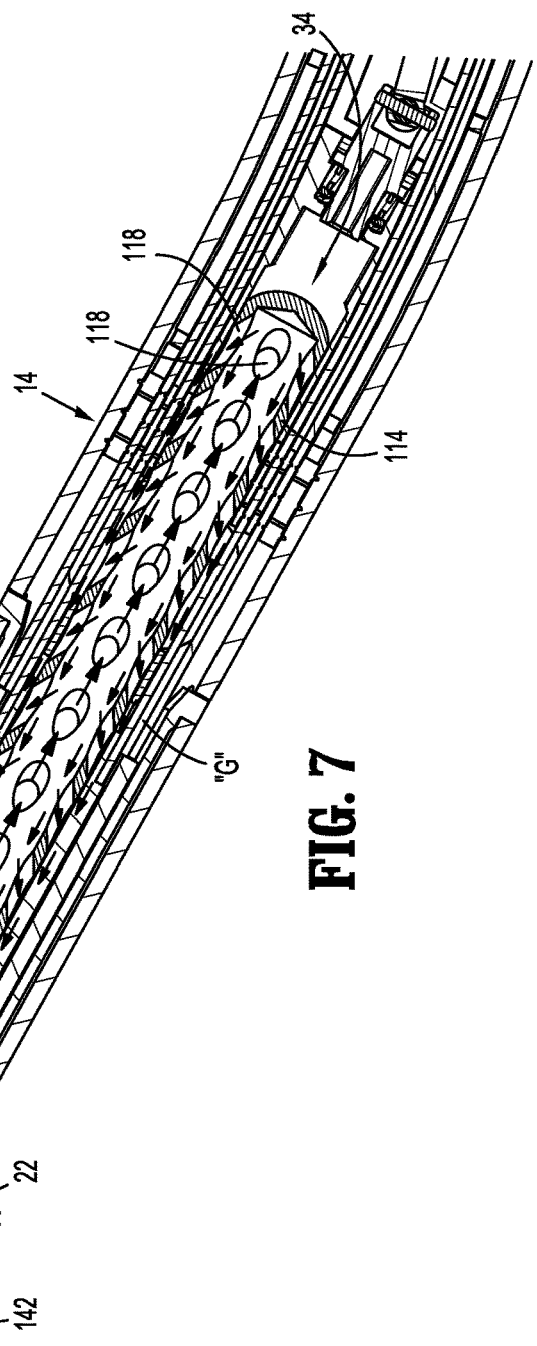

CLEANING APPARATUS FOR SURGICAL INSTRUMENTS

BACKGROUND

1. Technical Field

The present disclosure relates to a cleaning apparatus for use with a surgical instrument. More specifically, the present disclosure relates to a dual-function cleaning apparatus for use with a circular stapling instrument.

2. Background of Related Art

Surgical stapling instruments having an end effector configured to clamp and suture tissue are well known in the medical arts. Typically, these instruments include a first jaw that supports an anvil assembly and a second jaw that supports a cartridge assembly which houses a plurality of staples. The first and second jaws are movable in relation to each other between spaced and approximated positions to clamp tissue between the jaws prior to firing the staples into the tissue. The first and second jaws may also support two part fasteners or first and second compression members that interact to suture tissue.

Circular stapling instruments are used to perform end-to-end anastomosis procedures within a patient. During an end-to-end anastomosis procedure, an end of a first vessel portion is joined to an end of a second vessel portion. Typically, circular stapling instruments include an anvil, which defines an annular array of staple deforming depressions and an annular cartridge housing annular rows of staples. The annular cartridge is supported on a distal end of a hollow shaft. The hollow shaft houses components of approximation and firing mechanisms of the stapling instrument.

Some circular stapling instruments are designed to be disassembled after use to be cleaned or sterilized and then reassembled to be reused. During use of a circular stapling instrument, bodily fluid may enter the hollow shaft of the instrument and contaminate mechanisms of the instrument. Such contaminants may be difficult to effectively clean. Accordingly, a need exists for a cleaning apparatus to facilitate cleaning/sterilizing components of circular stapling instruments.

SUMMARY

One aspect of the present disclosure is directed to an apparatus for cleaning a surgical instrument. The apparatus includes an elongate member having a first end and a second end. The first end is configured for disposal within a cavity of a surgical instrument. The elongate member defines a longitudinal channel and a plurality of apertures extending transversely through the elongate member. The apertures are in communication with the longitudinal channel. The first end of the elongate member is configured to be coupled to a source of fluid. The longitudinal channel is configured to allow passage of fluid to the plurality of apertures.

In embodiments, the apertures may be configured to direct fluid toward the first end of the elongate member. The elongate member may define a longitudinal axis and each aperture defines an aperture axis. The longitudinal axis and the aperture axis intersect and define an angle β. The angle β may be between 0.1 degrees and 179.0 degrees. In some embodiments, the angle β may be between 1 and 90 degrees. Each aperture may have an inner opening communicating with longitudinal channel and an outer opening disposed adjacent an exterior surface of the elongate member. A portion of the outer openings are disposed closer to the first end of the elongate member than the respective inner openings.

In embodiments, each aperture may have a cylindrical configuration. It is contemplated that each aperture may be in the form of a slit.

In embodiments, the apparatus may include a cap supported on the first end of the elongate member. The cap may include a wall and a hood. The wall may extend radially from the elongate member. The hood may extend from the wall in a direction toward the second end of the elongate member. The hood may be configured to redirect fluid away from the first end of the elongate member. The hood may have a semi-circular configuration.

In embodiments, the cap may include a mating part configured to be coupled to a distal end of a surgical instrument. Upon coupling the mating part to the distal end of the surgical instrument, the second end of the elongate member is disposed distally of the distal end of the surgical instrument.

In embodiments, the mating part may include a cylindrical extension and a plurality of projections. The cylindrical extension may be disposed about the first end of the elongate member. The cylindrical extension and the elongate member may define a space. The projections may extend from the cylindrical extension into the space. It is envisioned that the cylindrical extension may have an outer surface defining a depression.

In another aspect of the present disclosure, a surgical system is provided. The surgical system includes a surgical instrument and an apparatus for cleaning the surgical instrument. The surgical instrument includes a distal end configured to be coupled to an end effector. The distal end defines a longitudinal cavity. The apparatus includes an elongate member having a first end and a second end. The second end is configured for disposal within the cavity of the surgical instrument. The elongate member defines a longitudinal channel and a plurality of apertures extending transversely through the elongate member. The apertures are in communication with the longitudinal channel. The first end of the elongate member is configured to be coupled to a source of fluid. The longitudinal channel is configured to allow passage of fluid to the plurality of apertures and into the cavity of the surgical instrument.

In embodiments, the apertures may be configured to direct fluid toward the first end of the elongate member and the distal end of the surgical instrument.

In embodiments, a cap of the apparatus may include a mating part configured to be coupled to the distal end of the surgical instrument such that upon coupling the mating part to the distal end of the surgical instrument, the second end of the elongate member is disposed distally of the distal end of the surgical instrument and encloses a trocar extending distally from the distal end of the surgical instrument.

In embodiments, the mating part may define a space configured for disposal of the distal end of the surgical instrument. A projection of the mating part may be configured to be coupled to a mating part of the distal end of the surgical instrument.

In embodiments, the surgical instrument may be a circular stapler.

In yet another aspect of the present disclosure, a method of using a surgical system is provided. The method includes disposing an elongate member of an apparatus within a cavity formed in a distal end of a surgical instrument. Fluid is dispensed into a first end of the elongate member such that the fluid moves through a longitudinal channel defined by the elongate member and through apertures defined transversely through the elongate member into the cavity of the surgical instrument.

In embodiments, the method may further include coupling the first end of the elongate member to the distal end of the surgical instrument. Upon coupling the first end of the elongate member to the distal end of the surgical instrument, a second end of the elongate member may be disposed distally of the distal end of the surgical instrument to enclose a trocar extending distally from the distal end of the surgical instrument.

In embodiments, the method may further include removing the second end of the elongate member from within the cavity of the surgical instrument prior to coupling the first end of the elongate member to the distal end of the surgical instrument. In embodiments, the method may further include removing a trocar of the surgical instrument from within the cavity of the surgical instrument prior to disposing the elongate member within the cavity of the surgical instrument. The method may further include disengaging an anvil and a cartridge from the surgical instrument prior to disposing the elongate member within the cavity of the surgical instrument.

BRIEF DESCRIPTION OF THE DRAWINGS

Various embodiments of the presently disclosed cleaning apparatus are described herein with reference to the drawings, wherein:

FIG. 6 is an enlarged view of the cleaning apparatus of FIG. 2 engaged to the adapter assembly of FIG. 2 in a first orientation;

FIG. 7 is a cross sectional view taken along line 7-7 of FIG. 6 with the cleaning apparatus connected to a source of fluid;

DETAILED DESCRIPTION OF EMBODIMENTS

Persons skilled in the art will understand that the instruments and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the described embodiments. Accordingly, the disclosure is not to be limited by what has been particularly shown and described, except as indicated by the appended claims.

As used herein, the term distal refers to that portion of the instrument which is farthest from a clinician, while the term proximal refers to that portion of the instrument which is closest to the clinician. In addition, as used herein, the term clinician refers to medical staff including doctors, nurses and support personnel.

The present disclosure is directed to a cleaning apparatus, described in detail below, which includes an elongate member having a first end and a second end configured for disposal in a cavity of a surgical instrument, such as, for example, a surgical stapling instrument. The elongate member defines a longitudinal channel and a plurality of apertures extending transversely through the elongate member. The first end of the elongate member is both configured to be coupled to a source of fluid, for example, cleaning fluid, to clean the surgical instrument, and a distal end of the surgical instrument to encase a trocar of the surgical instrument, as described in further detail below. Additional advantages of the presently disclosed cleaning apparatus are described below.

Figure 1:
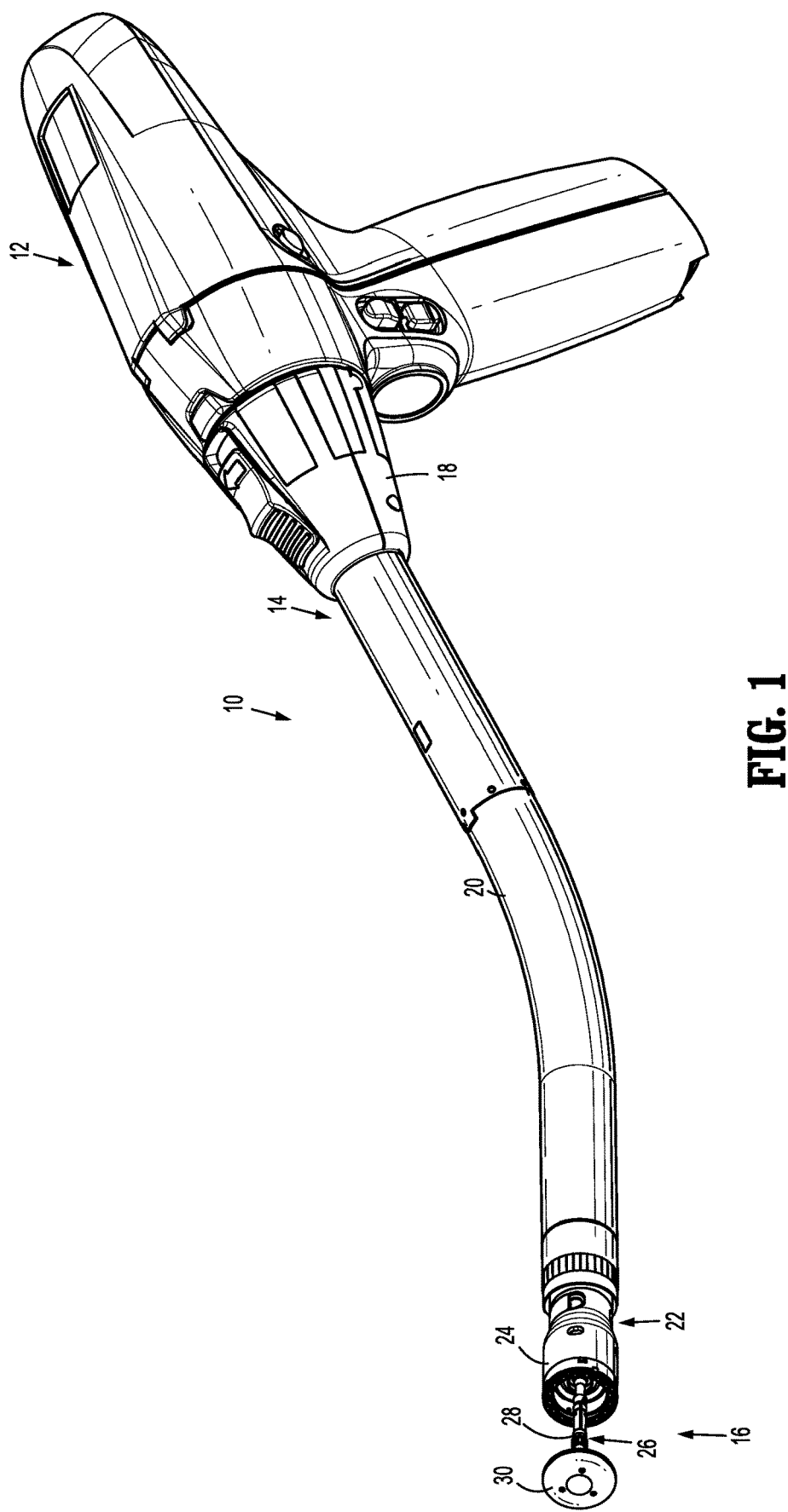
FIG. 1 is a perspective view of a surgical stapling instrument including a handle assembly, an adapter assembly, and an end effector in an unapproximated or spaced position.

FIG. 1 illustrates an embodiment of a surgical stapling instrument according to the present disclosure, referenced generally as a circular stapler 10. Circular stapler 10 includes a handle assembly 12, an adapter assembly 14 which is supported by and extends distally from the handle assembly 12, and an end effector 16 supported on a distal end 22 of adapter assembly 14. Adapter assembly 14 is reusable and includes a knob housing 18 that is releasably coupled to a distal end of handle assembly 12 and an elongated body portion 20 that extends distally from knob housing 18. Elongated body portion 20 has a distal end 22 that is configured to be coupled to a cartridge assembly 24 of end effector 16 and also to be coupled to a cleaning apparatus 100 (FIG. 10), as described in further detail below. Adapter assembly 14 converts a rotation of drive elements (not shown) of handle assembly 12 into axial movement of driven members (not shown) of adapter assembly 14 to actuate functions of end effector 16. A similar adapter assembly is disclosed in U.S. Patent Application Publication No. 2013/0324978 by Nicholas et al., which is incorporated herein in its entirety by reference. In some embodiments, circular stapler 10 may have an elongated body portion that is integrally formed with a manually actuable handle assembly 12 instead of an adapter assembly. One example of such a stapler is disclosed in U.S. Pat. No. 7,802,712 to Milliman et al., which is incorporated herein in its entirety by reference.

Circular stapler 10 further includes a trocar 32 (FIG. 9), which extends from a longitudinal cavity 34 (FIG. 7) defined in distal end 22 of elongated body portion 20. A proximal end of trocar 32 is configured to be removably coupled to an approximation mechanism (not shown) of adapter assembly 14. As known in the art, the approximation mechanism (not shown) is operable to selectively longitudinally move trocar 32 within cavity 34 to move an anvil assembly 26, which is supported on trocar 32, between unapproximated and approximated positions, in relation to cartridge assembly 24.

A distal end 36 (FIG. 9) of trocar 32 extends distally from distal end 22 of elongated body portion 20 upon assembly of trocar 32 with adapter assembly 14.

End effector 16 includes a cartridge assembly 24 and an anvil assembly 26. Cartridge assembly 24 is releasably mounted to distal end 22 of elongated body portion 20 of circular stapler 10 and is configured to discharge staples into tissue after approximation of cartridge assembly 24 and anvil assembly 26. In disclosed embodiments, cartridge assembly 24 is removably secured to distal end 22 of elongated body portion 20 such that cartridge assembly 24, or a portion thereof, may be replaced and circular stapler 10 may be reused. In other embodiments, only a portion of cartridge assembly 24 is configured to be removed, and subsequently replaced or reloaded. It is envisioned that cartridge assembly 24 may be operably mounted to a distal end of any actuation assembly, powered or manual, of various surgical instruments.

Anvil assembly 26 includes, inter alia, an anvil center rod 28 and an anvil head 30 supported on anvil center rod 28. A proximal end of anvil center rod 28 is dimensioned to releasably receive distal end 36 of trocar 32 to sec assembly 26 to circular stapler 10. As such, longitudinal movement of trocar 32, via an actuation of handle assembly 12, results in a corresponding longitudinal movement of anvil head 30 relative to cartridge assembly 24 to clamp tissue between cartridge and anvil assemblies 24, 26. Reference may be made to U.S. Pat. No. 7,802,712 to Milliman et al. for a detailed description of the construction and operation of an end effector including a cartridge assembly and an anvil assembly similar to that disclosed herein, which is incorporated by reference above.

Figure 2:
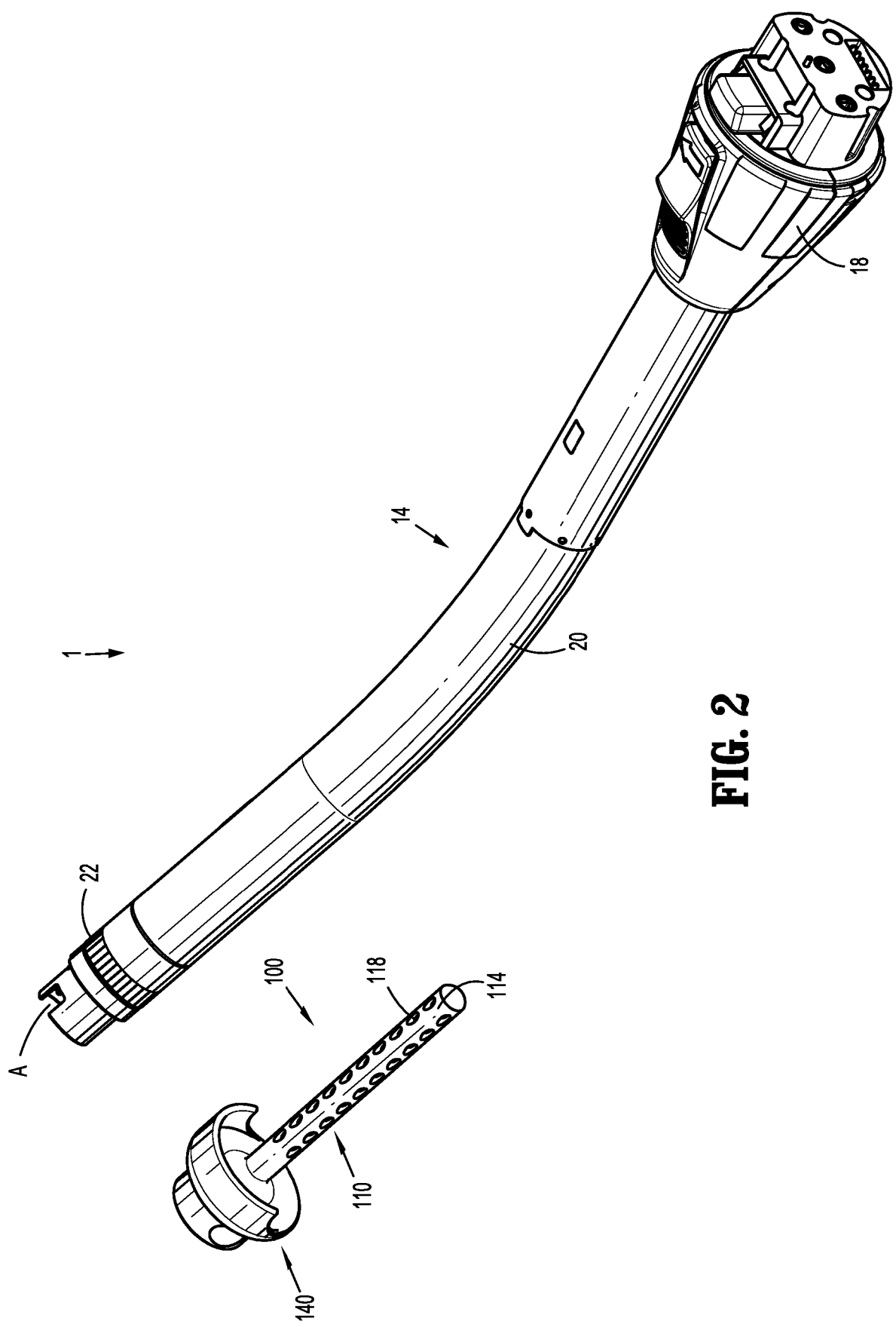
FIG. 2 is a perspective view of a surgical system including the adapter assembly of FIG. 1 and one embodiment of the presently disclosed cleaning apparatus prior to insertion of the cleaning apparatus into the adapter assembly.
Figure 10:
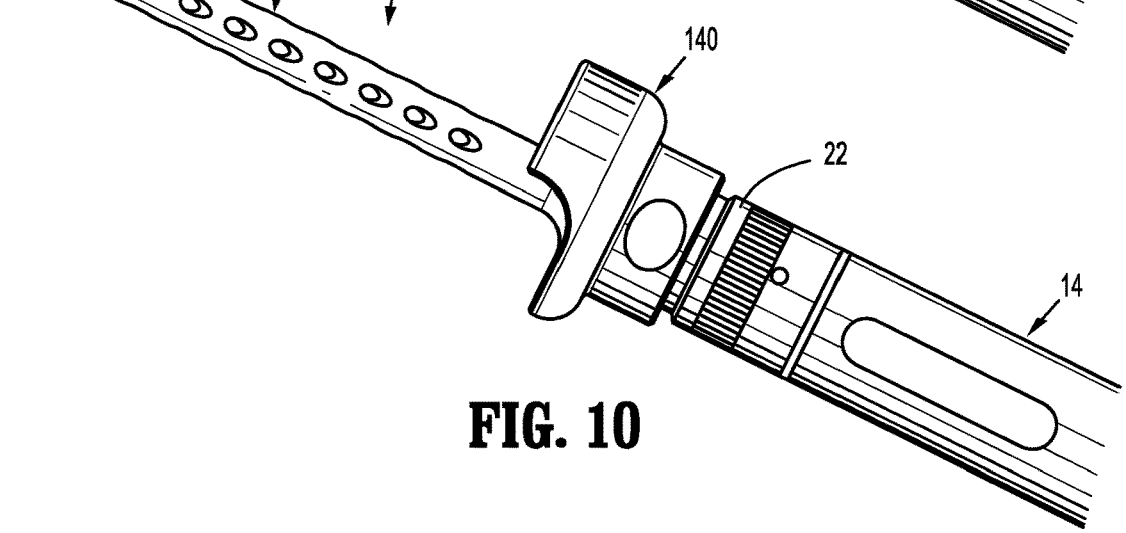
FIG. 10 is a side, perspective view of the cleaning apparatus of FIG. 2 engaged to the adapter assembly of FIG. 2 in a second orientation.

With reference to FIGS. 1 and 2, a surgical system 1 includes components of circular stapler 10 (i.e., handle assembly 12, adapter assembly 14, and/or end effector 16) and a cleaning apparatus 100 for cleaning circular stapler 10. Cleaning apparatus 100 is configured to engage distal end 22 of adapter assembly 14 in one of a first orientation, as shown in FIGS. 6 and 7, in which cleaning apparatus 100 is used to clean circular stapler 10, and a second orientation, as shown in FIG. 10, in which cleaning apparatus 100 is used as a trocar tip protector, as will be described in detail below.

Figure 3:
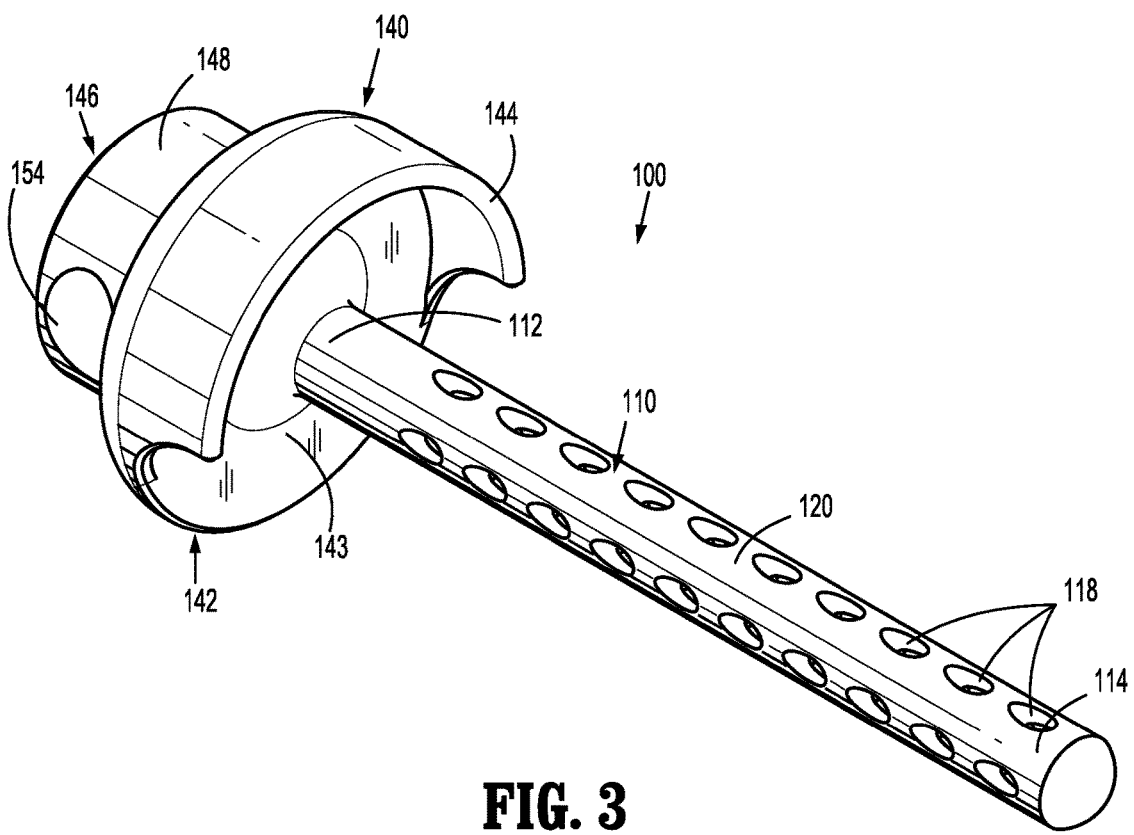
FIG. 3 is a side, perspective view of the cleaning apparatus of FIG. 2 from a second end of the cleaning apparatus.
Figure 4:
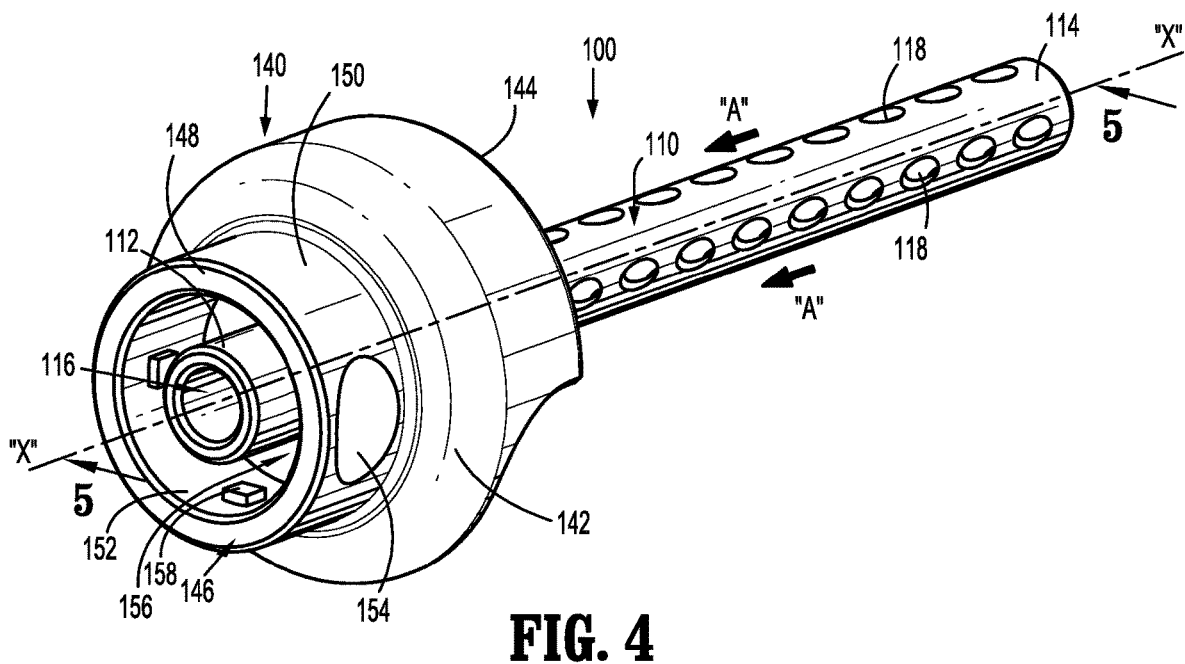
FIG. 4 is a side, perspective view of the cleaning apparatus of FIG. 2 from a first end of the cleaning apparatus.
Figure 5:
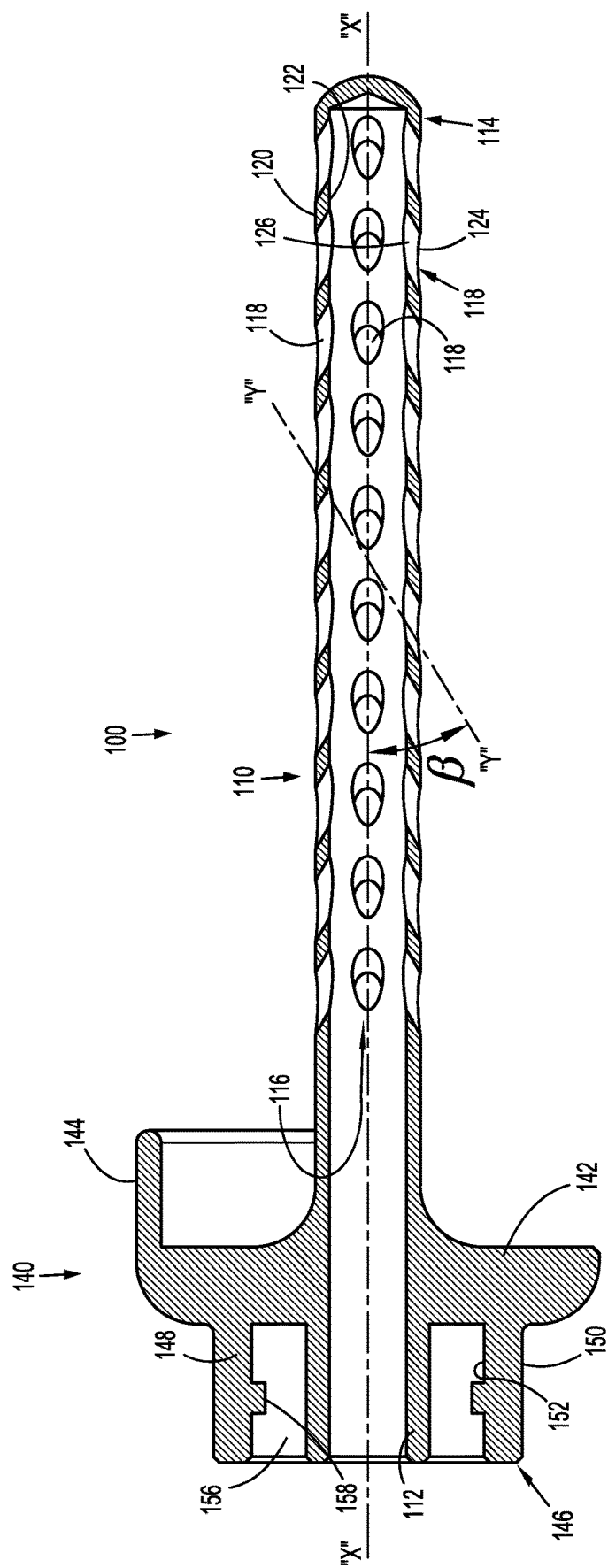
FIG. 5 is a cross sectional view taken along line 5-5 of FIG. 4.

With reference to FIGS. 3, 4, and 5, cleaning apparatus 100 generally includes an elongate member 110 and a cap 140 supported thereon. Elongate member 110 defines a longitudinal axis "X" and has a first end 112 (FIG. 4) and a second end 114. Elongate member 110 defines a longitudinal channel 116 that extends between first and second ends 112, 114 along longitudinal axis "X." Longitudinal channel 116 is dimensioned to receive trocar 32 of adapter assembly 14 such that elongate member 110 encases trocar 32. First end 112 of elongate member 110 is open and second end 114 of elongate member 110 is closed. In some embodiments, second end 114 of elongate member 110 may be open or define an aperture such that fluid can pass through second end 114.

First end 112 of elongate member 110 is configured to be coupled to a source of fluid, such as, for example, a fluid dispensing device 130 (FIG. 7). It is contemplated that first end 112 of elongated member 110 may be configured to connect to various fluid dispensing devices using a variety of fastening techniques, such as, for example, luer taper, threaded engagement, friction-fit, snap-fit, or the like, such that fluid, indicated by arrows "F," may be supplied through first end 112 of elongate member 110 under pressure into longitudinal channel 116. In some embodiments, an outer and/or inner surface 150, 152 of a cylindrical extension 148 that surrounds first end 112 of elongate member 110 may be configured to connect to various fluid dispensing devices.

With reference to FIG. 5, elongate member 110 further defines a plurality of apertures 118 in fluid communication with longitudinal channel 116. Apertures 118 extend transversely from longitudinal channel 116 through an outer surface 120 of elongate member 110. Apertures 118 are disposed along at least a portion of a length of elongate member 110, e.g., along an entire length of elongate member 110. In some embodiments, apertures 118 are aligned in longitudinal, parallel rows. Alternately, apertures 118 can be arranged in different patterns, e.g., a spiral pattern, in concentric rows about elongate member 110, or randomly formed along elongate member 110. Apertures 118 may have a cylindrical configuration and be configured to direct fluid from within longitudinal channel 116, out of elongate member 110, and toward first end 112 of elongate member 110, in the general direction indicated by arrow "A" in FIG. 4. In some embodiments, apertures 118 may assume a variety of shapes, such as, for example, triangular, square, rectangular, arcuate, tapered, oblong, polygonal, or the like. In addition, one or more spiral cut grooves or channels may be substituted for the apertures 118. Further, any combination of apertures, or apertures and channels, uniformly distributed or non-uniformly distributed about the elongate member 110 may be provided.

In particular, with continued reference to FIG. 5, in some embodiments, each aperture 118 defines an axis "Y," which extends at an acute angle β relative to longitudinal axis "X" of elongate member 110. In embodiments, angle β is between 0 degrees and 90 degrees. As such, fluid within longitudinal channel 116 flowing in a direction from first end 112 to second end 114 of elongate member 110 will be directed from apertures 118 in a direction toward first end 112 of elongate member 110. By discharging fluid in a direction toward first end 112, contaminants disposed within elongated body portion 20 of circular stapler 10 can be forced from elongated body portion 20. It is envisioned that in embodiments, it may be beneficial to direct fluid proximally from apertures 118. As such, angle β may also exceed 90 degrees, e.g., angle β may be between 90 degrees and 180 degrees.

Each aperture 118 has an outer opening 124 and an inner opening 126. Outer openings 124 are disposed adjacent an exterior of elongate member 110 and are contiguous with outer surface 120 of elongate member 110. Inner openings 126 are disposed adjacent longitudinal channel 116 and are contiguous with inner surface 122 of elongate member 110. Due to apertures 118 being angled relative to longitudinal axis "X" and directed toward first end 112 of elongate member 110, outer openings 124 of each aperture 118 are disposed closer to first end 112 of elongate member 110 than are respective inner openings 126.

With reference to FIGS. 3-8, cleaning apparatus 110 further includes a cap 140, which is supported about first end 112 of elongate member 110. For example, cap 140 may be integrally formed with elongate member 110 or secured to elongate member 110 using a variety of different fastening techniques, including, e.g., welding, crimping, etc. Cap 140 includes a wall 142 having a planar configuration and extending radially from first end 112 of elongate member 110. In embodiments, wall 142 may have a concave surface 143 oriented toward second end 114 of elongate member 118 to facilitate redirecting fluid toward second end 114. A hood 144 extends from wall 142 in a direction toward second end 114 of elongate member 110. Hood 144 has an arcuate configuration, e.g., a semi-circular configuration, to partially surround first end 112 of elongate member 110. In embodiments, hood 144 may be a full circle that extends from the periphery of wall 142 and completely surrounds first end 112 of elongate member 110. Hood 144 is configured to redirect fluid away from first end 112 of elongate member 110 toward second end 114 after fluid has been expelled from apertures 118. As such, hood 144 acts as a splash guard so that fluid can be collected, in a controlled manner, outside of elongate member 110 and elongated body portion 20 in a disposal area (not shown).

Cap 140 includes a mating part 146 configured to be coupled to a distal end of a surgical instrument, for example, distal end 22 of adapter assembly 14, when cleaning apparatus 100 is in the second orientation. In particular, mating part 146 includes a cylindrical extension 148 disposed about first end 112 of elongate member 110. Cylindrical extension 148 extends from wall 142 of cap 140 in a direction opposite to that of hood 144. Cylindrical extension 148 has an outer, arcuate surface 150 and an inner, arcuate surface 152. Outer surface 150 defines at least one depression 154, which may assume a variety of shapes, such as, for example, scalloped-shaped or concave. In addition, depression 154 may be textured to enhance a clinician's ability to grip and rotate cap 140.

An inner surface 152 of mating part 146 and first end 112 of elongate member 110 define an annular space 156. Annular space 156 is dimensioned for receipt of distal end 22 of adapter assembly 14. A plurality of projections 158 extend from inner surface 152 of cylindrical extension 148 into space 156 to facilitate securement of cleaning apparatus 100 to distal end 22 of adapter assembly 14. For example, projections 158 may be configured to be releasably secured, in a bayonet-type connection (i.e., inserted and rotated), within a cutout 23 (FIG. 9) formed in distal end 22 of adapter assembly 14. In some embodiments, cap 140 of cleaning apparatus 100 may be releasably coupled to distal ends of various circular staplers in various alternative fastening engagements, for example, those alternatives described herein.

When cleaning apparatus 100 is secured, in the second orientation, to circular stapler 10, as shown in FIG. 10, elongate member 110 is releasably attached to distal end 22 of adapter assembly 14 via the mating engagement between mating part 146 of cleaning apparatus 100 and mating part 23 of distal end 22 of adapter assembly 14. In some embodiments, first end 112 of elongate member 110, rather than mating part 146 of cap 140, may be configured to be coupled to distal end 22 of adapter assembly 14. As shown in FIG. 10, upon coupling mating part 146 of cleaning apparatus 100 to distal end 22 of adapter assembly 14, second end 114 of elongate member 110 is disposed distally of distal end 22 of adapter assembly 14 and is no longer disposed within longitudinal cavity 34 of adapter assembly 14.

With reference to FIGS. 6 and 7, to clean/sterilize circular stapler 10, cartridge assembly 24 (FIG. 1), anvil assembly 26 (FIG. 1) and trocar 32 (FIG. 9) are disassembled from adapter assembly 14. With trocar 32 removed from within longitudinal cavity 34 of adapter assembly 14, longitudinal cavity 34 is made available for receipt of elongate member 110 of cleaning apparatus 100. Cleaning apparatus 100 is oriented in the first orientation and second end 114 of elongate member 110 is inserted within longitudinal cavity 34 of adapter assembly 14. In this position, first end 112 of elongate member 110 is disposed distally of distal end 22 of adapter assembly 14 such that wall 142 of cap 140 is engaged to distal end 22 of adapter assembly 14. Cutouts "A" formed in distal end 22 of adapter assembly 14 allow fluid to escape from distal end 22 of adapter assembly 14 and exit longitudinal cavity 34 of adapter assembly 14.

In use, a source of fluid 130 is coupled to first end 112 of elongate member 110 of cleaning apparatus 100 and fluid, such as, for example, water or a cleaning solution "F," is dispensed into first end 112 of elongate member 110. Although not shown, first end 112 of elongate member 110 may include structure, e.g., internal threads, to facilitate coupling to a fluid source. Fluid "F" moves from first end 112 of elongate member 110, through longitudinal channel 116, to second end 114 of longitudinal channel 116 and through apertures 118 at angle β relative to longitudinal axis "X," as described above. After fluid "F" exits apertures 118, fluid "F" moves in a direction toward first end 112 of elongate member 110 and distal end 22 of adapter assembly 14 through a longitudinal gap "G" defined between outer surface 120 of elongate member 110 and an inner surface of distal end 22 of adapter assembly 14 to clean longitudinal cavity 34 of adapter assembly 14. Thereafter, fluid "F," now carrying contaminants or surgical debris, e.g., bodily fluid or tissue, passes out of longitudinal cavity 34 through cutouts "A" formed in distal end 22 of elongated body portion 20. After fluid "F" exits adapter assembly 14, fluid "F" contacts hood 144 of cap 140 of cleaning apparatus 100 and is redirected in a proximal direction, as indicated by arrow "B" in FIG. 7, toward a disposal area (not shown).

After circular stapler 10 is sufficiently clean, cleaning apparatus 100 can be removed from distal end 22 of adapter assembly 14 and discarded or reused and cartridge assembly 24, anvil assembly 26, and trocar 32 can be reassembled to adapter assembly 14 in preparation for reuse of circular stapler 10.

Figure 8:
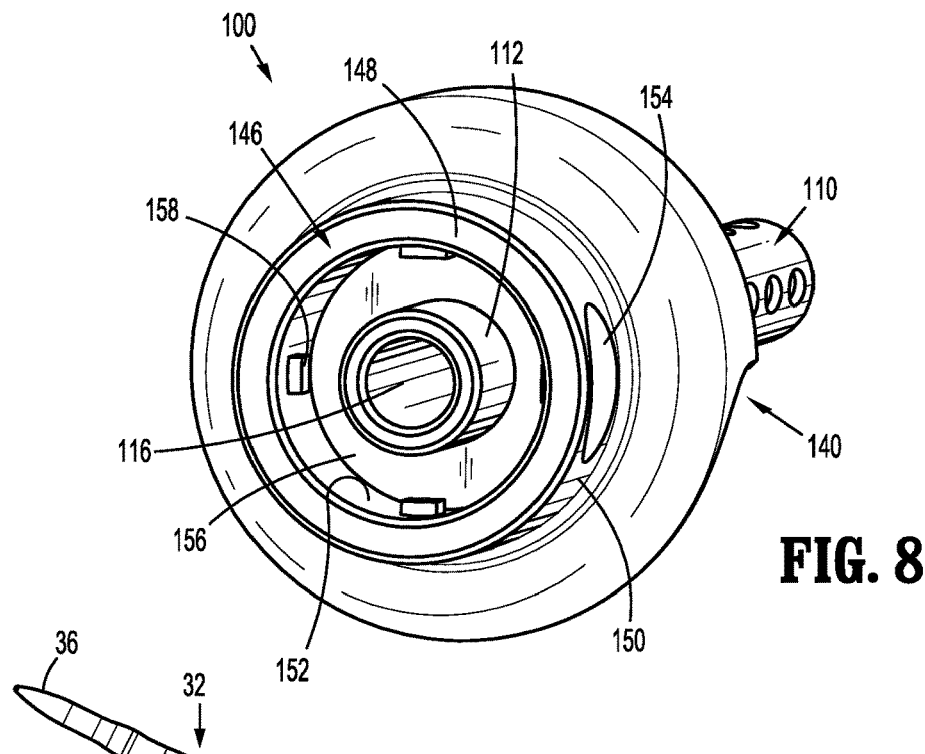
FIG. 8 is perspective view of a first end of the cleaning apparatus of FIG. 2.
Figure 9:
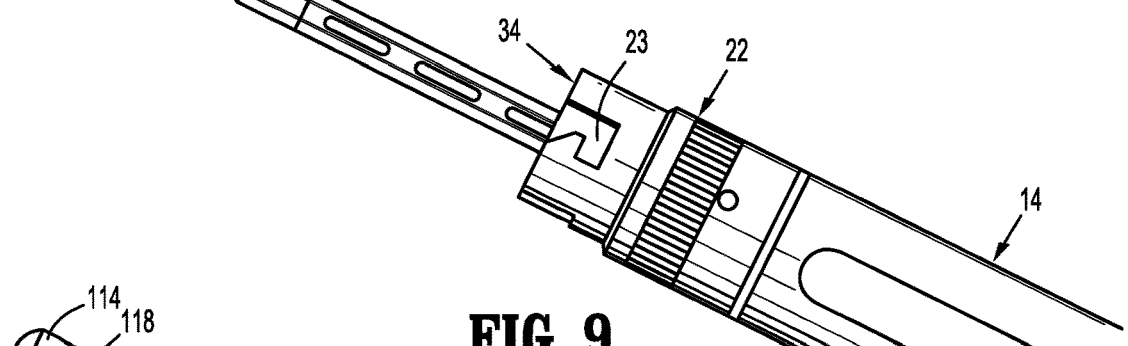
FIG. 9 is a side, perspective view of a distal end of the adapter assembly of FIG. 2 having a trocar extending therefrom.

With reference to FIGS. 8-10, cleaning apparatus 100 may be turned 180 degrees from the first orientation to the second orientation, as shown in FIG. 10. In the second orientation, cleaning apparatus 100 serves as a trocar tip protector. More specifically, as shown in FIG. 9, trocar 32 extends distally from distal end 22 of adapter assembly 14. After cartridge assembly 24 (FIG. 1) is disconnected from mating part 23 of distal end 22 of adapter assembly 14, elongate member 110 is positioned about trocar 32. Projections 158 of mating part 146 of cleaning apparatus 100 are inserted within cutouts 23 of distal end 22 of adapter assembly 14 and cleaning apparatus 100 is rotated in relation to adapter assembly 14 to releasably attach cleaning apparatus 100 to circular stapler 10. With cleaning apparatus 100 attached to circular stapler 10 in the second orientation, trocar 32 is completely enclosed by elongate member 110 to prevent trocar 32 from causing injury to medical personnel during non-use of circular stapler 10.

Figure 11:
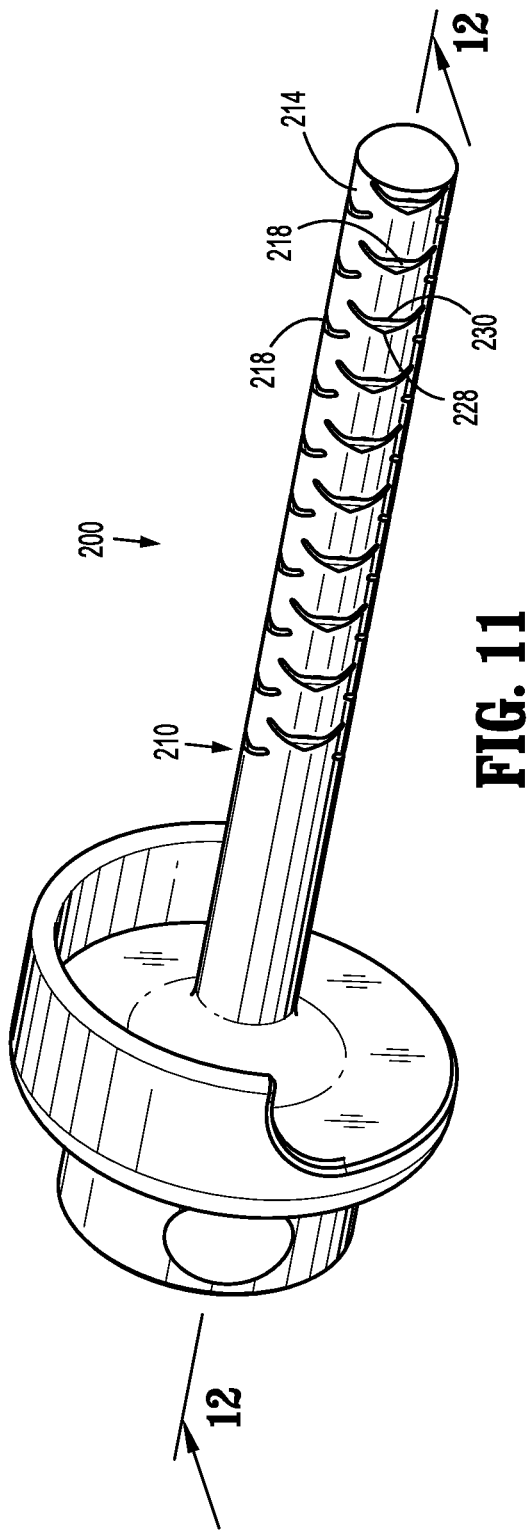
FIG. 11 is a perspective view of another embodiment of the presently disclosed cleaning apparatus for use with the surgical stapling instrument of FIG. 1.
Figure 12:
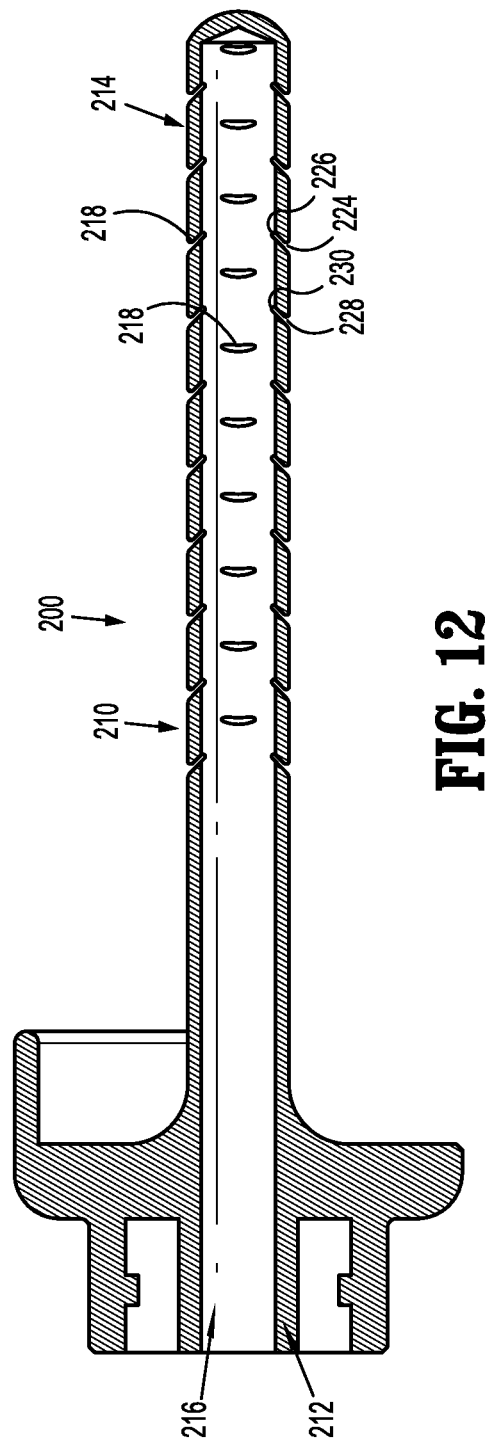
FIG. 12 is a cross sectional view taken along line 12-12 of FIG. 11.

FIGS. 11 and 12 illustrate another embodiment of a cleaning apparatus shown generally as 200. Cleaning apparatus 200 is similar to cleaning apparatus 100 described above and includes an elongate member 210 having a first end 212 and a second end 214 and defines a longitudinal channel 216 extending between first and second ends 212, 214. Instead of elongate member 210 having holes shaped like the apertures 118 of cleaning apparatus 100 described above, cleaning apparatus 200 defines a plurality of slits 218 extending transversely through elongate member 210. Similar to apertures 118 of cleaning apparatus 100 described above, slits 218 are also configured to direct fluid from within longitudinal channel 216, out of elongate member 210, and toward first end 212 of elongate member 210.

Slits 218 have an arcuate configuration as shown in FIG. 11 and a uniform cross-sectional configuration as shown in FIG. 12. Slits 218 may assume a variety of shapes, such as, for example, those alternatives described above with regard to the apertures 118. Slits 218 each have an outer opening 224 disposed adjacent an exterior surface of elongate member 210 and an inner opening 226 communicating with longitudinal channel 216. Each Slit 218 has a length defined between respective outer and inner openings 224, 226 and a thickness defined between upper and lower surfaces 228, 230. In embodiments, slits 218 are shaped such that the length of each slit 218 is greater than its thickness, e.g., the length is at least twice the thickness. In embodiments, slits 218 are dimensioned to generate a high velocity spray, which is directed into an inner surface of elongated body portion 20 of adapter assembly 14.

Cleaning apparatus 200 can be used in a similar manner as cleaning apparatus 100. Specifically, cleaning apparatus 200 has a dual function of both cleaning distal end 22 of adapter assembly 14, when positioned in a first orientation, and serving as a trocar tip protector, when positioned in a second orientation.

In some embodiments, cleaning apparatus 100 or 200 may be used with any surgical instrument having a hollow shaft.

Persons skilled in the art will understand that the instruments and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An apparatus for cleaning a surgical instrument, comprising:
    an elongate member having a first end and a second end, the second end being configured for disposal within a cavity of the surgical instrument, the elongate member defining:
        a longitudinal channel; and
        a plurality of apertures extending transversely through the elongate member and communicating with the longitudinal channel, the plurality of apertures being configured to direct fluid toward the first end of the elongate member;
    wherein the first end of the elongate member is configured to be coupled to a source of fluid, wherein the longitudinal channel is configured to allow passage of fluid to the plurality of apertures.

2. The apparatus according to claim 1, wherein the elongate member defines a longitudinal axis and each of the plurality of apertures defines an aperture axis, the longitudinal axis and the aperture axis intersecting and defining an angle, wherein the angle is between 0.1 degrees and 179.9 degrees.

3. The apparatus according to claim 2, wherein the angle is between 1 degree and 90 degrees.

4. The apparatus according to claim 1, wherein each aperture of the plurality of apertures has an inner opening communicating with the longitudinal channel and an outer opening disposed adjacent an exterior surface of the elongate member, at least a portion of the outer opening being disposed closer to the first end of the elongate member than the inner opening.

5. The apparatus according to claim 1, further comprising a cap supported on the first end of the elongate member.

6. The apparatus according to claim 5, wherein the cap includes:
    a wall extending radially from the elongate member; and
    a hood extending from the wall in a direction toward the second end of the elongate member, the hood being configured to redirect fluid away from the first end of the elongate member.

7. The apparatus according to claim 5, wherein the cap includes a mating part configured to be coupled to a distal end of the surgical instrument such that upon coupling the mating part to the distal end of the surgical instrument, the second end of the elongate member is disposed distally of the distal end of the surgical instrument.

8. A surgical system, comprising:
    a surgical instrument having a distal end configured to be coupled to an end effector, the distal end defining a longitudinal cavity; and
    an apparatus for cleaning the surgical instrument, the apparatus including:
        an elongate member having a first end and a second end, the second end being configured for disposal within the longitudinal cavity of the surgical instrument, the elongate member defining:
            a longitudinal channel; and
            a plurality of apertures extending transversely through the elongate member and communicating with the longitudinal channel, wherein the first end of the elongate member is configured to be coupled to a source of fluid, wherein the longitudinal channel is configured to allow passage of fluid to the plurality of apertures and into the longitudinal cavity of the surgical instrument; and
        a cap supported on the first end of the elongate member, the cap having a mating part configured to be coupled to the distal end of the surgical instrument such that upon coupling the mating part to the distal end of the surgical instrument, the second end of the elongate member is disposed distally of the distal end of the surgical instrument and encloses a trocar extending distally from the distal end of the surgical instrument.

9. The surgical system according to claim 8, wherein the plurality of apertures are configured to direct fluid toward the first end of the elongate member and the distal end of the surgical instrument.

10. The surgical system according to claim 9, wherein the elongate member defines a longitudinal axis and each of the plurality of apertures defines an aperture axis, the longitudinal axis and the aperture axis intersecting and defining an angle, wherein the angle is between 0.1 degrees and 179.9 degrees.

11. The surgical system according to claim 10, wherein the angle is between 1 degree and 90 degrees.

12. The surgical system according to claim 9, wherein each aperture of the plurality of apertures has an inner opening communicating with the longitudinal channel and an outer opening disposed adjacent an exterior surface of the elongate member, at least a portion of the outer opening being disposed closer to the first end of the elongate member than the inner opening.

13. The surgical system according to claim 8, wherein the cap includes:
    a wall extending radially from the elongate member; and
    a hood extending from the wall in a direction toward the second end of the elongate member, the hood being configured to redirect fluid away from the first end of the elongate member and the distal end of the surgical instrument.

14. The surgical system according to claim 8, wherein the mating part includes:
a cylindrical extension disposed about the first end of the elongate member, the cylindrical extension and the elongate member defining a space configured for disposal of the distal end of the surgical instrument; and
at least one projection extending from the cylindrical extension into the space, the at least one projection configured to be coupled to a corresponding mating part of the distal end of the surgical instrument.

\* \* \* \* \*